(12) United States Patent
Reimels (10) Patent No.: US 10,201,342 B2
(45) Date of Patent: Feb. 12, 2019

(54) RADIO TRANSPARENT RETRACTOR SYSTEM AND METHOD OF USING RADIO TRANSPARENT RETRACTOR SYSTEM

(71) Applicant: Alphatec Spine, Inc., Carlsbad, CA (US)

(72) Inventor: William Reimels, Oceanside, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 69 days.

(21) Appl. No.: 15/168,859

(22) Filed: May 31, 2016

(65) Prior Publication Data
US 2016/0345951 A1 Dec. 1, 2016

Related U.S. Application Data

(60) Provisional application No. 62/169,130, filed on Jun. 1, 2015.

(51) Int. Cl.
*A61B 17/02* (2006.01)
*A61B 6/12* (2006.01)

(52) U.S. Cl.
CPC .............. *A61B 17/025* (2013.01); *A61B 6/12* (2013.01); *A61B 2017/0256* (2013.01); *A61B 2017/0287* (2013.01)

(58) Field of Classification Search
CPC ..................................................... A61B 1/32
See application file for complete search history.

(56) References Cited

U.S. PATENT DOCUMENTS

| | | | |
|---|---|---|---|
| 6,364,832 B1 * | 4/2002 | Propp | A61B 1/303 600/201 |
| 6,464,634 B1 * | 10/2002 | Fraser | A61B 17/0293 600/233 |
| 8,262,570 B2 * | 9/2012 | White | A61B 17/0293 600/219 |
| 9,380,932 B1 * | 7/2016 | Lynn | A61B 1/32 |
| 9,655,505 B1 * | 5/2017 | Gharib | A61B 1/32 |
| 9,737,287 B2 * | 8/2017 | Gifford | A61B 17/02 |
| 9,737,288 B2 * | 8/2017 | Karpowicz | A61B 17/0206 |
| 2002/0055670 A1 * | 5/2002 | Weiss | A61B 1/32 600/220 |
| 2002/0193666 A1 * | 12/2002 | Sherts | A61B 17/0293 600/231 |
| 2003/0069477 A1 * | 4/2003 | Raisman | A61B 1/303 600/220 |

(Continued)

*Primary Examiner* — Jan Christopher Merene
(74) *Attorney, Agent, or Firm* — Honigman Miller Schwartz and Cohn LLP (57) ABSTRACT

A retractor system for use in spinal surgical procedures includes at least two retractor blades, each of the at least two retractor blades, a shim and a shim inserter. The shim has an expansion band and the shim inserter is configured to slide the shim between and along the at least two retractor blades and dispose the shim at a distal end of the at least two retractor blades. The shim spreads the at least two retractor blades away from each other when the shim insert slides the shim between and along the at least two retractor blades and the shim prevents the distal end of each of the at least two retractor blades from closing in on each other due to musculature load when the shim is disposed at the distal end of the at least two retractor blades.

10 Claims, 9 Drawing Sheets

(56) References Cited

U.S. PATENT DOCUMENTS

| | | | |
|---|---|---|---|
| 2004/0049099 A1* | 3/2004 | Ewers ...................... A61B 1/32 | 600/206 |
| 2004/0116777 A1* | 6/2004 | Larson ................... A61B 17/02 | 600/210 |
| 2005/0059866 A1* | 3/2005 | Bjork ..................... A61B 17/02 | 600/227 |
| 2005/0080321 A1* | 4/2005 | Bjork ....................... A61B 1/32 | 600/230 |
| 2005/0149035 A1* | 7/2005 | Pimenta ................... A61B 1/32 | 606/86 R |
| 2005/0215862 A1* | 9/2005 | Larson ..................... A61B 1/32 | 600/201 |
| 2006/0052672 A1* | 3/2006 | Landry .............. A61B 17/0293 | 600/233 |
| 2006/0069315 A1* | 3/2006 | Miles ................... A61B 5/0488 | 600/219 |
| 2006/0122463 A1* | 6/2006 | Klaassen .................. A61B 1/32 | 600/221 |
| 2006/0155170 A1* | 7/2006 | Hanson .................. A61B 17/02 | 600/201 |
| 2006/0224043 A1* | 10/2006 | Guinan ................... A61B 1/303 | 600/220 |
| 2006/0287583 A1* | 12/2006 | Mangiardi ............. A61B 17/02 | 600/208 |
| 2007/0038216 A1* | 2/2007 | Hamada ................. A61B 17/02 | 606/53 |
| 2007/0219416 A1* | 9/2007 | Perez-Cruet ........... A61B 17/02 | 600/219 |
| 2008/0058606 A1* | 3/2008 | Miles ....................... A61B 1/32 | 600/214 |
| 2008/0097164 A1* | 4/2008 | Miles ....................... A61B 1/32 | 600/219 |
| 2008/0154296 A1* | 6/2008 | Taylor ..................... A61B 1/32 | 606/190 |
| 2009/0112061 A1* | 4/2009 | Kim ................... A61B 1/00177 | 600/109 |
| 2009/0124860 A1* | 5/2009 | Miles ..................... A61B 17/02 | 600/202 |
| 2010/0094137 A1* | 4/2010 | Furlong ................. A61B 1/042 | 600/477 |
| 2010/0114147 A1* | 5/2010 | Biyani ..................... A61B 1/32 | 606/191 |
| 2011/0196208 A1* | 8/2011 | Warren .................... A61B 1/32 | 600/210 |
| 2012/0088979 A1* | 4/2012 | Nunley ................ A61B 17/025 | 600/231 |
| 2012/0232349 A1* | 9/2012 | Perrow .................... A61B 1/32 | 600/201 |
| 2014/0005484 A1* | 1/2014 | Charles ................. A61B 17/02 | 600/201 |
| 2014/0135584 A1* | 5/2014 | Lee .................... A61B 5/04001 | 600/202 |
| 2014/0350347 A1* | 11/2014 | Karpowicz ........ A61B 17/0206 | 600/215 |
| 2015/0305731 A1* | 10/2015 | Friedrich ............... A61B 90/30 | 600/216 |
| 2015/0351738 A1* | 12/2015 | Perrow ............. A61B 17/0293 | 600/226 |
| 2016/0015374 A1* | 1/2016 | Gifford .............. A61B 17/3415 | 600/201 |
| 2016/0192922 A1* | 7/2016 | Friedrich ........... A61B 17/0206 | 600/214 |
| 2017/0095243 A1* | 4/2017 | Perrow ............. A61B 17/0293 | |
| 2017/0143325 A1* | 5/2017 | Lynn .................. A61B 17/0218 | |
| 2017/0156580 A1* | 6/2017 | Miles ....................... A61B 1/32 | |
| 2017/0258315 A1* | 9/2017 | Gharib ..................... A61B 1/32 | |

\* cited by examiner

RADIO TRANSPARENT RETRACTOR SYSTEM AND METHOD OF USING RADIO TRANSPARENT RETRACTOR SYSTEM

RELATED APPLICATION

This application claims priority to U.S. Provisional Patent Application Ser. No. 62/169,130 filed Jun. 1, 2016, the entirety of which is incorporated herein by reference.

TECHNICAL FIELD

The application generally relates to the field of spinal orthopedics, and more particularly to tissue retractor systems having radio transparent retractor blades and methods of using tissue retractor systems to retract soft tissue during surgical procedures.

BACKGROUND

The spine is a flexible column formed of a plurality of bones called vertebrae. The vertebrae are hollow and piled one upon the other forming a strong hollow column for support of the cranium and trunk. Various spinal disorders such as scoliosis, neuromuscular disease, and cerebral palsy may cause the spine to become misaligned, curved, and/or twisted or result in fractured and/or compressed vertebrae. It is often necessary to introduce an interbody device to fuse adjacent vertebra together to help correct the spinal disorder.

The introduction of an interbody device such as an implant, may be done using a minimally invasive procedure with a lateral approach. In general, minimally invasive procedures use a retractor. The retractor includes a plurality of retractor blades which cooperate with each other to form a generally tubular opening. The retractor blades are inserted into the body and radially displaced from each other so as to form a surgical corridor leading from a small incision on the skin to the surgical site.

Currently, retractors include at least two retractor blades which when closed together form a cylindrical tube. The retractor is introduced into the surgical site and gradually expanded by positioning the retractor blades apart from one another. A tremendous load is placed on the distal end of the retractor blades by surrounding muscles and ligaments, a phenomena known as "musculature load." Musculature load works to bend the retractor blades and close the distal end of the surgical corridor. Accordingly, the retractor blades are currently formed of a durable and rigid metal to help withstand the musculature load. The interbody device is then passed through the surgical corridor. Since the window of view is narrow through the surgical corridor, it is known to use an x-ray machine to help guide the placement of the interbody device. However, the metallic retractor blades can interfere with the x-ray's ability to view the interbody device.

Accordingly, it remains desirable to have a retractor system configured to withstand the musculature load but have retractor blades which are radio transparent so as to facilitate the view of the interbody device by the x-ray machine.

SUMMARY

The embodiments described herein relate to retractor systems with x-ray transparent (also known as radio transparent) retractor blades that withstand musculature load. Also described herein are methods for performing a spinal procedure using retractor systems with radio transparent retractor blades that withstand musculature load and allow for enhanced monitoring of an interbody location and placement in a surgical site.

Retractor systems having a retractor with retractor blades formed of a radio transparent material and configured to withstand musculature load and methods of using the retractor systems are provided. In one exemplary embodiment, a retractor system includes a retractor. The retractor includes at least two retractor blades and a retractor blade support. The retractor blade support may be a ring having slots configured to support the retractor blades so as to allow the retractor blades to be displaced radially away from each other. The retractor blades are formed of a radio transparent material. The retractor blades may have an arcuate cross-section and are configured to form a tubular cross-section when closed onto each other. Accordingly, as the retractor blades are displaced radially from each other, the surgical corridor is enlarged.

Each retractor blade has a blade arm. The blade arm may be generally orthogonal to an axial length of the retractor blade and is configured to slidingly engage a respective slot of the retractor blade support.

A locking mechanism may be included and may have a locking ring with a dimension complimentary to the blade support. The locking mechanism includes a single central lock or a plurality of locks configured to lock the blade arms with respect to the retractor blade support. Thus, the locking mechanism is configured to lock the retractor blades in place relative to the retractor blade support and each other so as to form a desired surgical corridor.

A shim with an expansion band can be included. In one embodiment of the shim, an anchor is disposed on the expansion band. The expansion band is a generally circular member with at least one protrusion having an outer surface contoured to slidingly engage an inner surface of a retractor blade. The expansion band is configured to be disposed at the distal end of the retractor blades and can be made from a durable and rigid material such as a metallic material, a ceramic, a composite, etc. The anchor fixes the shim to the surgical site and the expansion band maintains a set distance between the distal ends of the retractor blades such that musculature load does not decrease the size of the surgical corridor at the distal end relative to the proximal end thus ensuring that the surgical corridor has a uniform opening along its length.

A shim inserter in the form of a generally elongated member with a distal end configured to engage the expansion band can be included. In embodiments, the distal end of the shim inserter has a lip configured to engage a top edge of the expansion band. By engaging the expansion band, the shim inserter can evenly slide the expansion band down and between the retractor blades into the surgical corridor. The proximal end of the shim inserter may include a head configured to receive blows from an instrument such as a hammer. Accordingly, the shim inserter may be used to both introduce the shim into the surgical site and to push the anchor so as to find purchase in bone material, e.g. a vertebra, or an annulus of an intervertebral disc and thereby fixing the expansion band in place.

The retractor system may further include a shim remover. The shim remover is an elongated member configured to slide within the surgical corridor. The shim remover includes a gripping member configured to engage the shim so as to remove the shim from the surgical site upon completion of the surgical procedure. In a preferred embodiment, the gripping member is configured to engage a receiving feature of the expansion band. The shim may also have a mechanism that locks the shim to the retractor blades so the shim is removed when the retractor is withdrawn from the patient.

A method of using the retractor system having a retractor with retractor blades formed of a radio transparent material is also provided. The method includes the step of introducing the retractor blades into the surgical site. The method proceeds to the step of x-ray monitoring the surgical site. The method proceeds to the step of inserting the shim onto the distal end of the shim inserter and introducing the shim into the surgical corridor formed by the retractor blades. The proximal end of the retractor blades may be contoured to facilitate insertion of the shim between the retractor blades. The retractor blades are radially displaced from each other by the insertion of the shim therebetween so as to form a surgical corridor having a desired dimension. The method proceeds to the step of driving the shim inserter and the shim into the surgical site so as to introduce the anchor into a vertebra or annulus of an intervertebral disc, and fixing the expansion band in place. The expansion band prevents the distal ends of the retractor blades from closing in on each other as a result of musculature load. The method proceeds to the step of introducing an interbody into the surgical site, through the surgical corridor and x-ray monitoring of the interbody.

Accordingly, the retractor system is configured to provide retractor blades which do not interfere with x-ray electromagnetic waves used to view the interbody while at the same time withstanding the musculature load so as to maintain a uniform surgical corridor.

Additional features and advantages of the radio transparent retractor systems described herein will be set forth in the detailed description which follows, and in part will be readily apparent to those skilled in the art from that description or recognized by practicing the embodiments described herein, including the detailed description which follows, the claims, as well as the appended drawings.

It is to be understood that both the foregoing general description and the following detailed description describe various embodiments and are intended to provide an overview or framework for understanding the nature and character of the claimed subject matter. The accompanying drawings are included to provide a further understanding of the various embodiments, and are incorporated into and constitute a part of this application. The drawings illustrate the various embodiments described herein, and together with the description serve to explain the principles and operations of the claimed subject matter.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be better understood when read in conjunction with the following drawings where like structure is indicated with like reference numerals and in which:

DETAILED DESCRIPTION

A retractor system having a retractor and a shim is provided. The retractor includes a radio transparent retractor blade so as to facilitate x-ray viewing of the surgical site. The shim is slid down the surgical corridor to the surgical site and is configured to withstand musculature load so as to maintain a uniform surgical corridor. A method of performing a spinal procedure using a retractor system with radio transparent retractor blades is also provided.

The retractor further includes a retractor blade support configured to support at least two retractor blades. Each of the retractor blades has a blade arm. The blade arm may be generally orthogonal to an axial length of the retractor blade and is configured to slidingly engage a slot of the retractor blade support. The retractor blade support is further configured to guide the blade arms along a common plane so as to allow the retractor blades to displace radially away from each other. The retractor blades are formed of a radio transparent material which does not obscure imaging from an x-ray machine.

The retractor system further includes a shim inserter. The shim includes an expansion band and an anchor. The expansion band has a peripheral wall dimensioned to correspond to a desired dimension of the surgical corridor. The shim is mounted to a distal end of the shim inserter. The shim inserter introduces the shim into the opening of the retractor blades and radially displaces the retractor blades away from each other so as to form the surgical corridor. Thus, the surgical corridor is formed by radio transparent retractor blades and is kept in a uniform in dimension by the expansion band. As the surgical corridor is radio transparent, an x-ray machine may clearly view or image the surgical site and the introduction of other devices such as an interbody implant.

Figure 1:
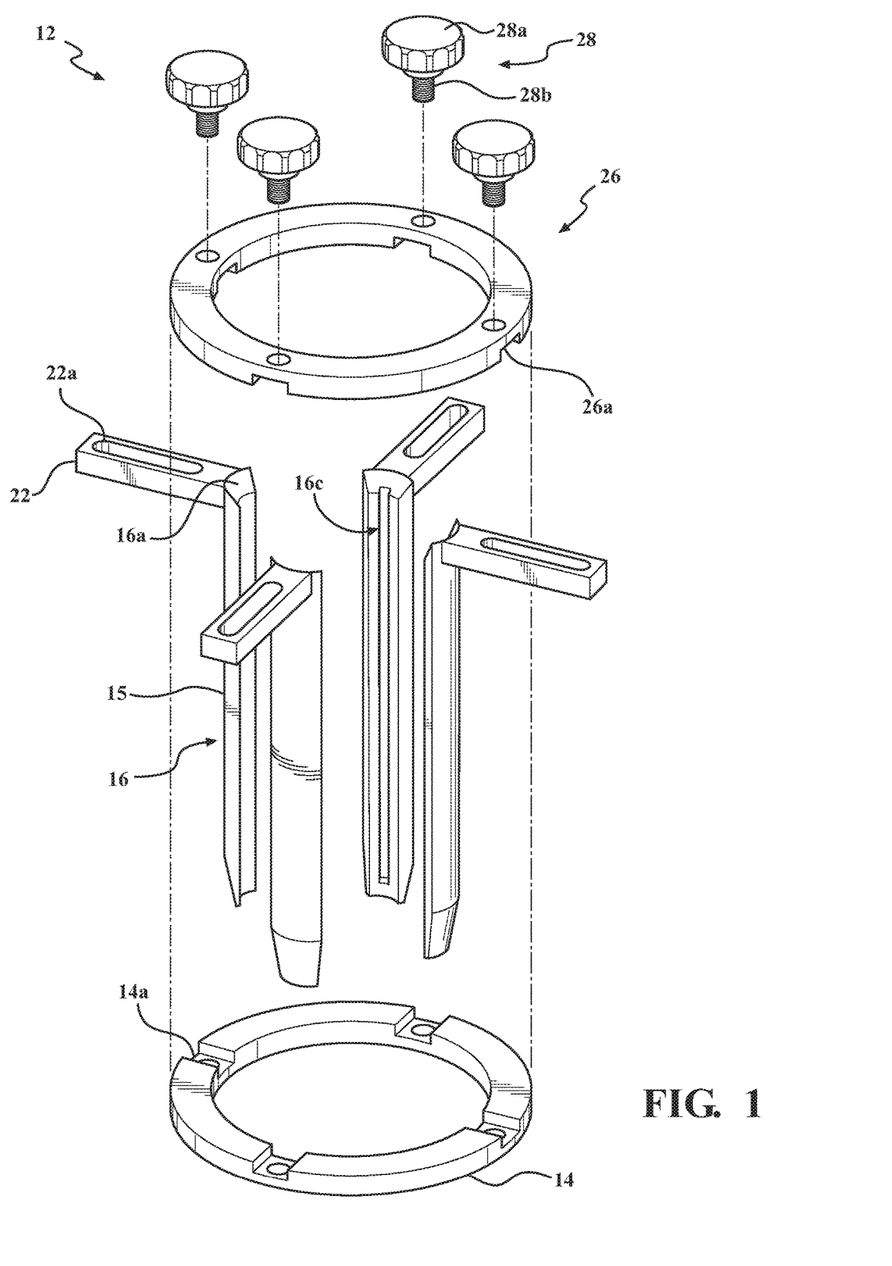
FIG. 1 schematically depicts an exploded perspective view of a tissue retractor according to one or more embodiments disclosed and described herein; [prior art]
Figure 2:
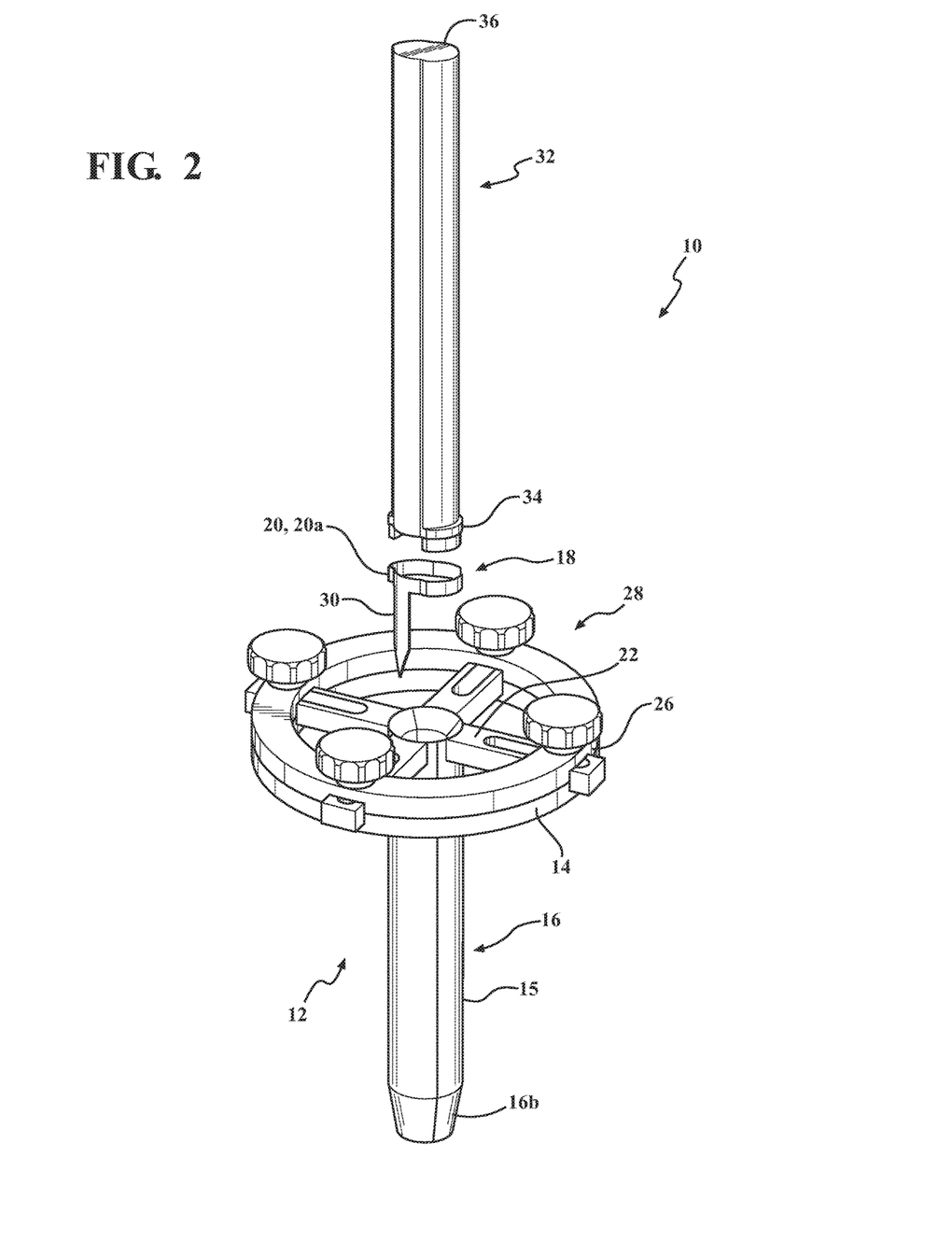
FIG. 2 schematically depicts a perspective view a tissue retractor system according to one or more embodiments disclosed and described herein.

Referring to FIGS. 1 and 2, an illustrative view of a retractor system 10 is provided. With reference first to FIG. 1, a retractor 12 has a retractor blade support 14 and at least two retractor blades 16. Each of the retractor blades 16 has a blade portion 15 and a blade arm 22. The blade portion 15 has a proximal end attached to the blade arm 22 and a distal end 16b. The blade arm 22 may be generally orthogonal to an axial length of a respective retractor blade 16. The retractor 12 includes a retractor blade support 14 in the form of a ring having slots 14a configured for the blade arms 22 to fit and slide therewithin. The blade arm 22 has a height greater than the depth of a slot 14a so as to protrude from a top surface of the retractor blade support 14. The blade arms 22 are configured to slidingly engage a respective slot 14a of the blade support 14, thereby supporting the retractor blades 16 and allowing the retractor blades 16 to be displaced radially away from each other. The retractor blade support 14 may be formed as a durable and rigid material such as a metallic material, illustratively including steel, stainless steel, titanium alloys, etc., or a ceramic material, a metal matrix composite material and the like. The retractor 12 shown and described herein is provided for illustrative purposes and is not intended to limit the scope of the appended claims. Any retractor previously, currently or hereafter made may be adapted for use with the shim and shim inserter described herein.

FIG. 1 shows a retractor 12 configured to support four retractor blades 16, however it should be appreciated that the retractor 12 may be configured to support at least two retractor blades 16, for example three retractor blades 16, and more than four retractor blades 16, for example five retractor blades 16, six retractor blades 16, etc. The retractor blades 16 are formed of a radio transparent material, such as a ceramic, a polymer such as polyether ether ketone (PEEK), a composite material such as fiber reinforced PEEK, etc. The retractor blades 16 have an arcuate cross-section and are configured to form a tubular cross-section between the retractor blades 16 when closed onto each other and as the retractor blades 16 are displaced radially from each other the surgical corridor widens.

The proximal end of each retractor blade 16 includes a chamfered edge 16a. The chamfered edge 16a facilitates the introduction of a shim 18 and assists an expansion band 20 of the shim 18 in radially displacing the retractor blades 16 away from each other. The outer surface of a distal end 16b of each retractor blade 16 is tapered so as to facilitate the introduction of the retractor blades 16 into a surgical site.

A locking mechanism 24 includes a locking ring 26 having a dimension complimentary to the retractor blade support 14. The locking ring 26 includes slots 26a configured to receive the top edge of a respective blade arm 22. The locking mechanism 24 includes a plurality of locks 28 configured to lock a respective blade arm 22 to the retractor blade support 14. The plurality of locks 28 are illustratively shown as a knob 28a having a leg 28b configured to engage an elongated slot 22a of a respective blade arm 22. The leg 28b may be threaded to engage a threaded bore in the slot 14a. The knobs 28a may be turned to pinch the blade arms 22 between the locking ring 26 and the retractor blade support 14 as shown in FIG. 2, thereby preventing the blade arm 22 from moving relative to the retractor blade support 14.

Figure 3A:
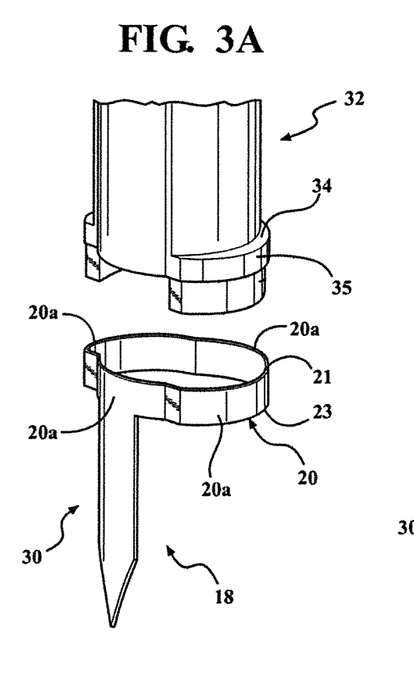
FIG. 3A schematically depicts a perspective view of a distal end of a shim inserter and a shim according to one or more embodiments disclosed and described herein.
Figure 3B:
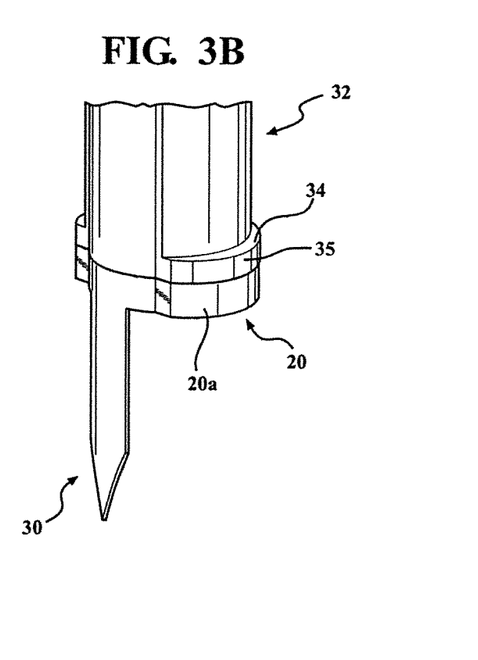
FIG. 3B schematically depicts a perspective view of the distal end of the shim inserter and the shim shown in FIG. 3A with the shim attached to the shim inserter.
Figure 3C:
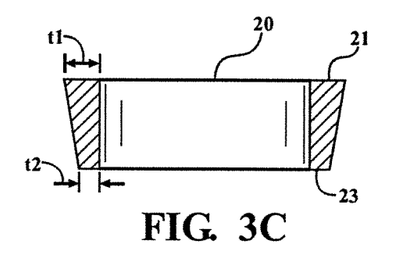
FIG. 3C schematically depicts a side cross-sectional view of a shim expansion band according to one or more embodiments disclosed and described herein.
Figure 3D:
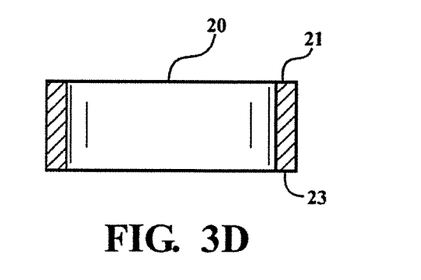
FIG. 3D schematically depicts a side cross-sectional view of a shim expansion band according to one or more embodiments disclosed and described herein.

With reference now to FIGS. 2-3D, an illustrative embodiment of the shim 18 is provided. The shim 18 includes an expansion band 20 and an anchor 30 extending from the expansion band 20. The expansion band 20 is a generally circular member formed of a durable and rigid material such as a metallic material, illustratively including steel, stainless steel, titanium alloys, etc., or a ceramic material, a metal matrix composite material and the like. The expansion band 20 includes one or more protrusions 20a having an outer surface contoured to slidingly engage an inner surface of a respective retractor blade 16. The anchor 30 is disposed on the expansion band 20. The expansion band 20 is configured to be disposed at the distal end of the retractor blades 16 and at the surgical site. The expansion band 20 may attach to one or more of the retractor blades 16 and slidingly engage one or more of the retractor blades 16. The anchor 30 includes a pointed end configured to assist in penetrating a vertebra or an annulus of an intervertebral disc. The anchor 30 fixes the shim 18 and the one or more attached retractor blades 16 to a surgical site and the expansion band 20 maintains a desired distance between the distal ends 16b of the retractor blades 16, i.e. the expansion band 20 overcomes musculature load on the retractor blades 16 so as to provide and maintain a surgical corridor having a uniform circumferential area.

Figure 4:
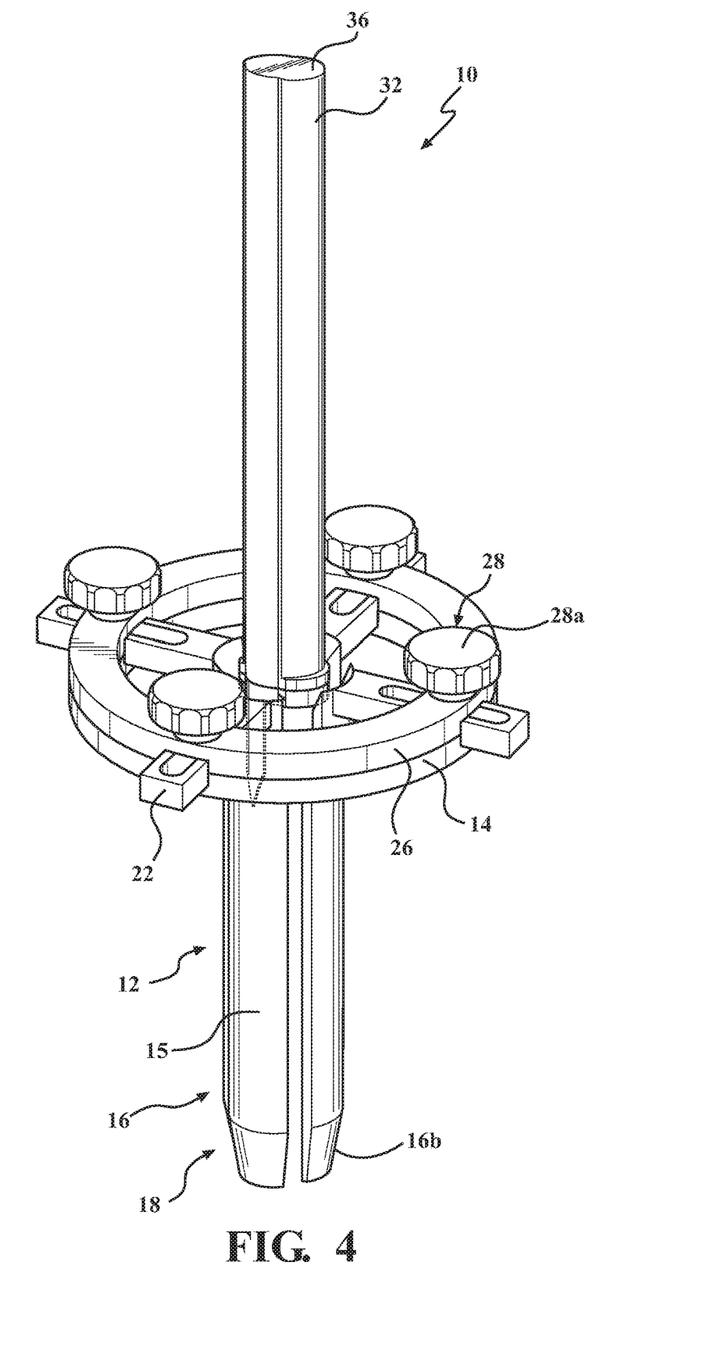
FIG. 4 schematically depicts a perspective view of a tissue retractor system with a shim inserter inserting a shim between retractor blades of a retractor according to one or more embodiments disclosed and described herein.

Referring to FIGS. 2-4, the expansion band 20 may include a plurality of protrusions 20a. The number of protrusions 20a may correspond to the number of retractor blades 16 the retractor 12 is configured to support. As shown, the illustrative example of the retractor 12 includes four retractor blades 16 and thus the expansion band 20 includes four protrusions 20a. The protrusions 20a are dimensioned to engage the chamfered edges 16a of the respective retractor blades 16. As shown in FIG. 4, as the expansion band 20 is introduced and pressed down between the retractor blades 16, the angle of the chamfered edge 16a assists the movement of the expansion band 20 from the proximal end to the distal end 16b of the retractor blades 16 and moves the retractor blades 16 away from each other, i.e. the surgical corridor between the retractor blades 16 is widened. FIG. 3C illustrates a side cross-sectional view of the expansion band having a tapered sidewall with a proximal edge 21 having a thickness t1 and a distal edge 23 having a thickness t2 which is less than the thickness t1. It should be appreciated that the tapered sidewall of the expansion band 20 illustrated in FIG. 3C has a wedge shape and assists in the introduction and pressing down of the expansion band 20 between the retractor blades 16 and can be sued with retractor blades 16 that do not have a chamfered edge 16a. In the alternative, the expansion band 20 may have a uniform thickness sidewall as illustrated in FIG. 3D with the proximal edge 21 having generally the same thickness as the distal edge 23.

Still referring to FIGS. 2-4, an illustrative view of a shim inserter 32 is provided. The shim inserter 32 is a generally elongated member. The shim inserter 32 may have a solid cylindrical body (not shown) or may include an elongated channel running the axial length of the body. A distal end of the shim inserter 32 includes a lip 34 configured to engage the top edge 21 of the expansion band 20 so as to evenly or uniformly slide the expansion band 20 down between the retractor blades 16, i.e. down the surgical corridor. The lip 34 has an outer surface 35 having contours dimensioned similar to the protrusions 20a so as to help distribute the load evenly across the top edge 21 of the expansion band 20. The proximal end of the shim inserter 32 may include a head 36 configured to receive the blows of an instrument such as a hammer. Generally, the head 36 is a planar surface. Accordingly, the shim inserter 32 may be used to both introduce the shim 18 into the surgical site and hammer the anchor 30 into the surgical site, fixing the expansion band 20 in place.

Figure 5:
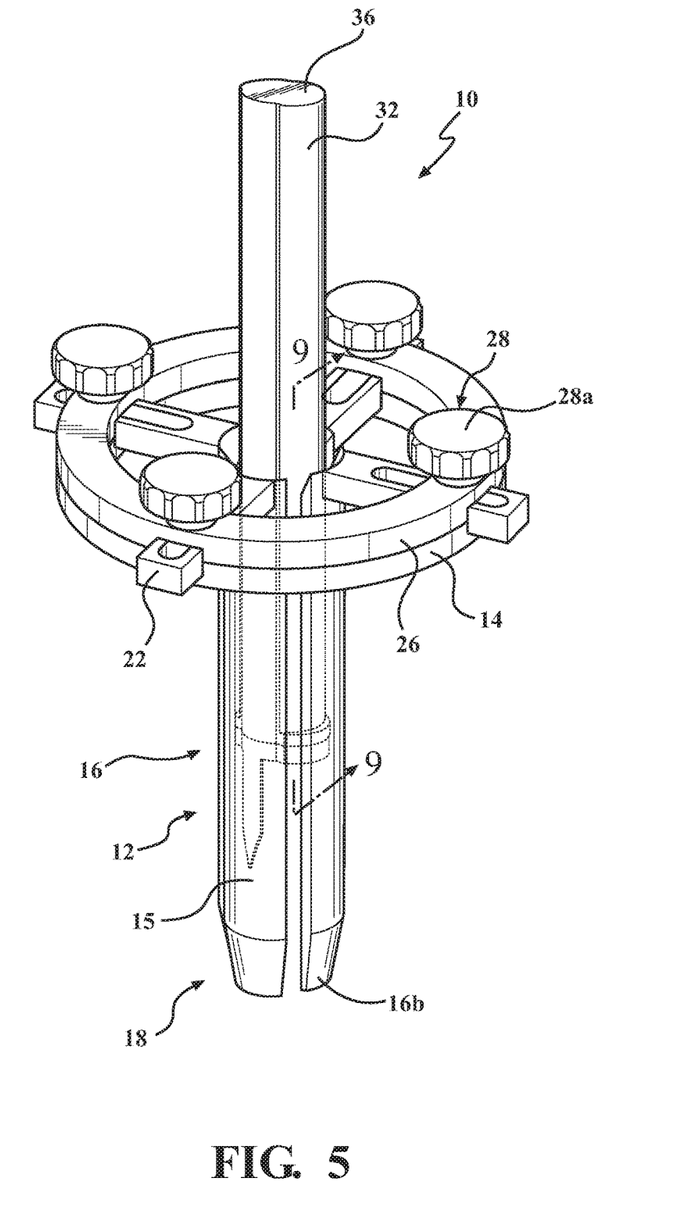
FIG. 5 schematically depicts a perspective view of the tissue retractor system shown in FIG. 4 with the shim inserter evenly sliding the shim between the retractor blades of the retractor according to one or more embodiments disclosed and described herein.
Figure 6:
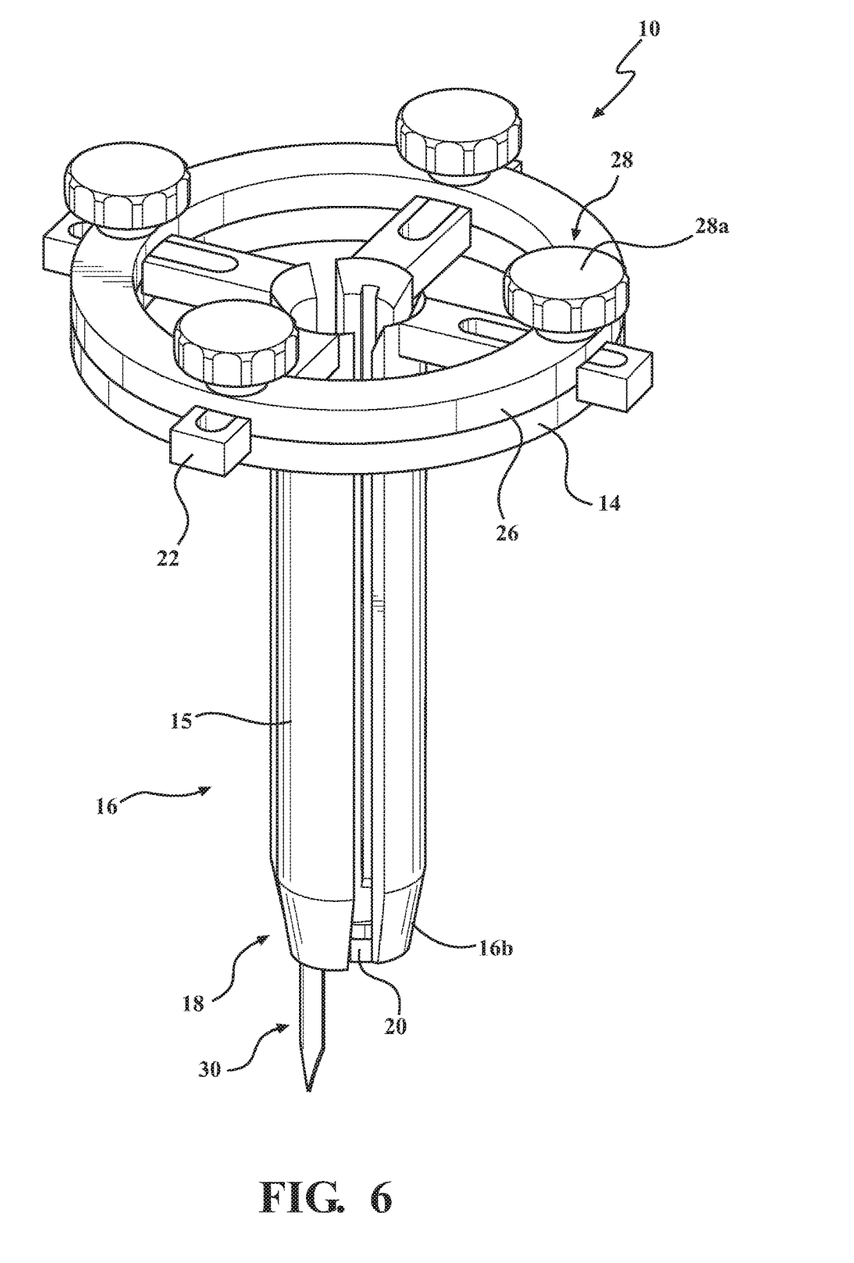
FIG. 6 schematically depicts a perspective view of the tissue retractor system shown in FIG. 4 with the shim positioned at the distal end of the retractor blades of the retractor according to one or more embodiments disclosed and described herein.
Figure 9:
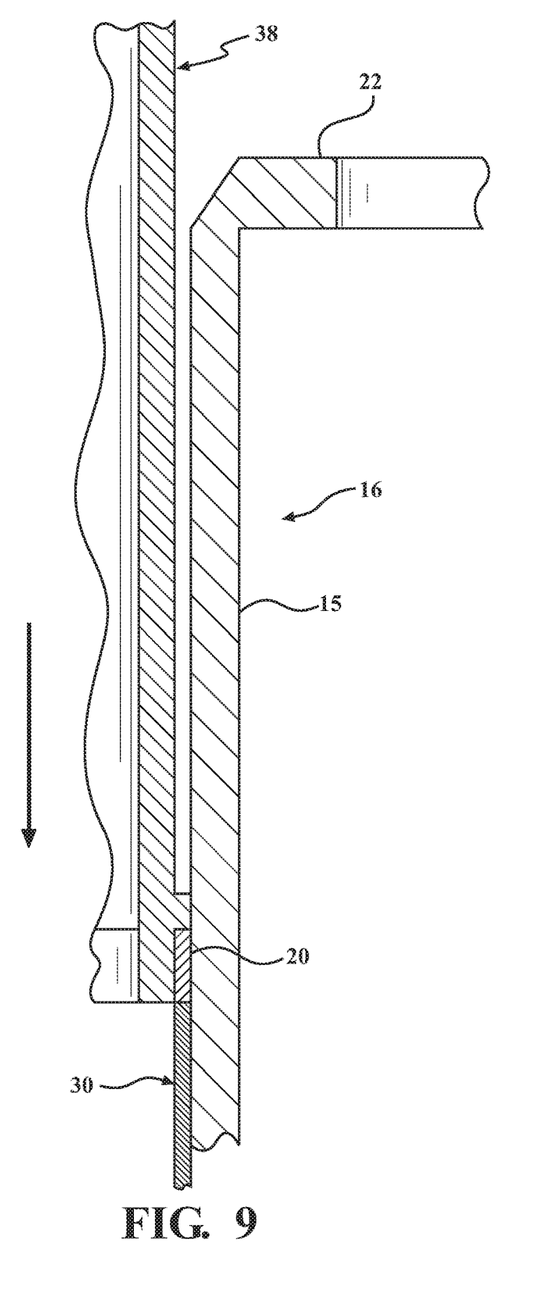
FIG. 9 schematically depicts a side cross-sectional view of section 9-9 shown in FIG. 5.

Referring to FIGS. 2-6 the shim 18 is introduced into an opening formed by retractor blades 16 using the shim inserter 32 as shown particularly in FIG. 4. FIG. 4 also illustrates that the retractor blades 16 may be locked into place once the shim 18 is introduce into the opening formed by the retractor blades. It should be appreciated that the distal end of the surgical corridor will be narrower than the proximal end of the surgical corridor due to the musculature load when the shim 18 is disposed adjacent the proximal end of the surgical corridor. As the shim 18 advances distally as illustrated in FIG. 5 the retractor blades 16 may be locked down at the proximal end via the locking mechanisms 24 to prevent collapsing of the surgical corridor at the proximal end. FIG. 5 illustrates the shim 18 shim located approximately half-way down the surgical corridor, and the retractor blades 16 having been moved apart from each other, e.g. compare FIG. 2 to FIG. 5. FIG. 9 illustrates a cross sectional view of section 9-9 shown in FIG. 5. Particularly, FIG. 9 illustrates the shim inserter 38 pushing the expansion band 20 and anchor 30 towards the distal end 16b (not shown) of the retractor blade 16. FIG. 6 illustrates the shim 18 positioned at the distal ends 16b of the retractor blades 16 and providing a surgical corridor with a desired opening. The surgical corridor opens to the circumferential area of the expansion band 20 as the shim 18 is slid to the distal end 16b of the retractor blades 16, overcomes the musculature load on the retractor blades 16, and displaces the retractor blades 16 outwardly from each other. The shim 18 determines the circumferential area of the surgical corridor formed by inner surfaces of the retractor blades as well as being a mechanism for spreading the retractor blades 16 apart. The circumference of the expansion band 20 is the linear distance around an inner surface of the expansion band 20. Thus, it should be appreciated that the expansion band 20 of the shim 18 has a circumference large enough to fit a predetermined interbody device.

After the shim 18 has been slid to the distal end 16b of the retractor blades 16 the anchor 30 may be driven into a vertebra or annulus of an intervertebral disc at the surgical site and the distal ends 16b of the retractor blades 16 are fixed relative to the surgical site and prevented from closing towards each other by the expansion band 20. FIG. 6 shows the retractor blades 16 evenly spaced apart along the entire surgical corridor which allows for the interbody to be introduced into the surgical site.

The retractor system 10 may be provided to the surgeon in a kit, wherein the kit contains a plurality of shims 18 each of different circumferences and a corresponding number of shim inserters 32 so as to provide the surgeon with multiple options based upon the size of the interbody being implanted. For example, should it be desired that a retractor 12 form a surgical corridor larger than what is shown in FIG. 4, a shim having the desired circumference (e.g. larger in circumference than what is shown in the figures) can be used.

Figure 7:
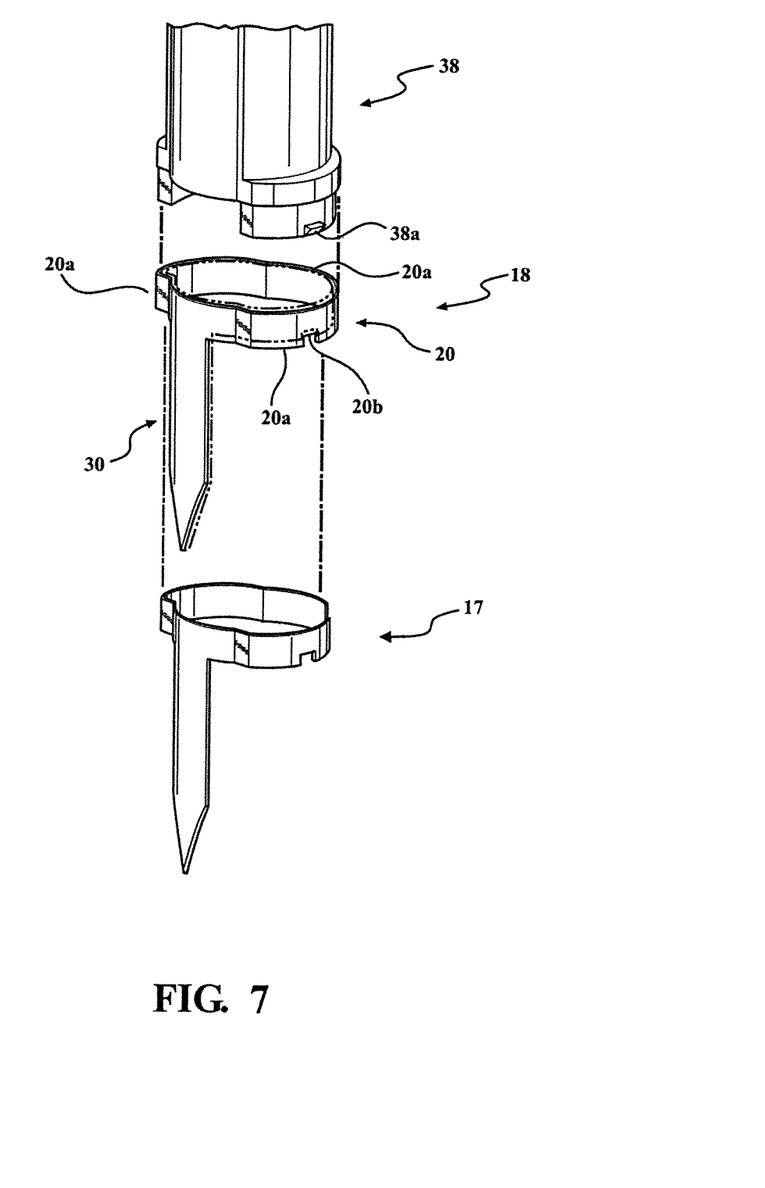
FIG. 7 schematically depicts a perspective view of a distal end of a shim retractor and a pair of shims according to one or more embodiments disclosed and described herein.

Referring now to FIG. 7, a shim remover 38 is provided. The shim remover 38 is an elongated member configured to slide within the surgical corridor. The shim remover 38 includes a gripping member 38a configured to engage the shim 18 so as to remove the shim 18 from the surgical site upon completion of the surgical procedure. In a preferred embodiment, the gripping member 38 is configured to engage a receiving feature 20b of the expansion band 20. In operation, the shim 18 is introduced into the opening formed by retractor blades 16 using the shim inserter 32 (FIG. 4), slid down between the retractor blades 16 (FIG. 5) and positioned at the distal end 16b. A force, e.g. a blow from a hammer, is applied to the proximal end 36 of the shim inserter 32 which is translated to the anchor 30 of the shim 18, thereby driving the anchor 30 into a vertebra or annulus of an intervertebral disc at the surgical site. After a surgical procedure has been completed, for example an interbody has been implanted at or within a surgical site; the shim remover 38 is introduced into the surgical corridor between the retractor blades 16. A distal end of the shim remover 38 is slid down the surgical corridor until the gripping member 38a is engaged with the receiving feature 20b of the expansion band 20 and the expansion band 20 with the anchor 30 is attached to the shim remover 38. The shim remover 38 with the expansion band 20 and anchor 30 attached thereto is withdrawn from the surgical corridor between the retractor blades 16. FIG. 7 also illustrates a first shim 17 with a first expansion band having a first circumference and the second shim 18 with the second expansion band 20 having second circumference, the second circumference being larger than the first circumference such that the second shim 18 can slide over the first shim 17 during a surgical procedure and provide an enlarge surgical corridor.

Figure 8:
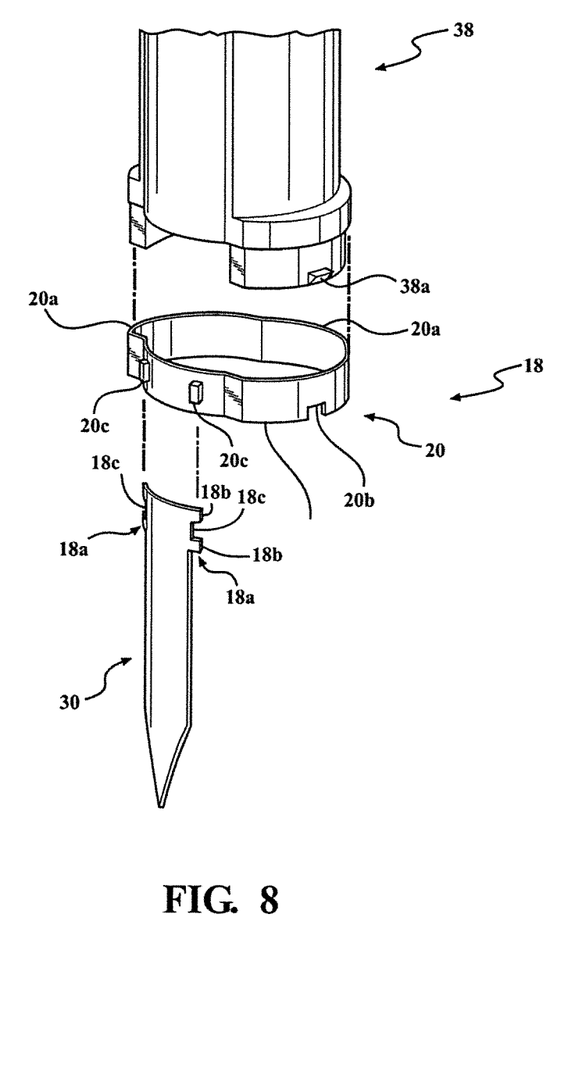
FIG. 8 schematically depicts a perspective view of a distal end of a shim retractor and a shim with a detachable anchor according to one or more embodiments disclosed and described herein.

Referring to FIG. 8, an embodiment of the shim 18 with the expansion band 20 and the anchor 30 being two separate pieces is shown. The anchor 30 includes an attachment portion 18a shown illustratively as a pair of spaced apart and opposite arms 18b extending opposite each other from a top edge of the anchor 30. Between the arms 18b is a slot 18b adapted to engage a corresponding tab 20c extending from the sidewall of the expansion band 20. The arms 18b, slot 18b and pins 20c provide a snap fit or interference fit between the anchor 30 and the expansion band 20. The anchor 30 may be introduced into the surgical site to stabilize the retractor 12. The expansion band 20 is introduced into the surgical corridor formed by the retractor blades 16, radially expanding the surgical corridor as the expansion band 20 is fed towards the surgical site. The expansion band 20 is then attached to the anchor 30 by having corresponding tabs 20c snap fit or interference fit with slots 18c between the respective pair of arms 18b. It should be appreciated that other attachment configurations can be used to attach the anchor 30 to the expansion band 30, illustratively snap fit attachment configurations, hook and loop attachment configurations and the like.

The shim 18 may further include a locking mechanism configured to lock the shim 18 to the retractor blades 16 so as to allow the shim 18 to be removed from the surgical site along with the retractor blades 16 and to prevent the shim 18 from slipping out from between the distal ends 16b of the retractor arms. For example, one of the tabs 20c extending from the expansion band 20 shown in FIG. 8 can slidingly engagement a groove 16c (FIG. 1) on an inner surface of a retractor blade 16. The groove 16c does not extend the entire length of the retractor blade 16, i.e. the groove 16c has a distal end surface 16d that prevents the tab 20c and thus the expansion band 20 from sliding off and beyond the distal end 16b of the retractor blade 16. Accordingly, when the retractor blades 16 are removed from the surgical site the shim 18 is removed also. It should be appreciated that any locking mechanism currently known and used in the art to attach two components together may be adapted and used to attach the shim 18 to one or more of the retractor blades 16.

A method of using the retractor system 10 having a retractor 12, a shim 18 and a shim inserter 32 is also provided. The retractor 12 includes retractor blades 16 formed of a radio transparent material. The method includes the step of introducing the retractor blades 16 into a surgical site. The method proceeds to the step of ensuring the locking mechanism 24 is disengaged before introducing the shim 18 and monitoring the surgical site with an x-ray machine. The retractor 12 may be used in conjunction with a dilator (not shown), the dilator is introduced into the body to create an opening. The retractor 12 is then slid onto the dilator with the retractor blades 16 in a closed and locked position (FIG. 2). Once the retractor 12 is slid into the surgical site, the locking mechanism 24 can be disengaged. The retractor 12 is opened to form a desired surgical corridor. The locking mechanism 24 may be engaged so as to fix the surgical corridor formed by the retractor blades 16. The method proceeds to the step of inserting the shim 18 onto the distal end of the shim inserter 32 (FIGS. 2, 3A, 3B) and introducing the shim 18 into the surgical corridor formed by the retractor blades 16 (FIG. 4). Musculature load closes the distal end of the retractor blades 16 towards each other, however introduction of the shim 18 down the surgical corridor forces the shim 18 to radially displace the retractor blades 16 away from each other so as to form a surgical corridor having a desired dimension. The method proceeds to the step of sliding the shim 18 into the surgical site and applying a force to the proximal end 36 of the shim inserter 32 so as to introduce the anchor 30 into a vertebra or intervertebral disc. The anchor 30 is embedded within the vertebra or intervertebral disc and fixes the expansion band 20 in place. The expansion band 20 prevents the distal ends 16b of the retractor blades 16 from closing in on each other as a result of musculature load. The method proceeds to the step of withdrawing the shim inserter 32 from the surgical corridor between the retractor blades 16 and introducing an interbody into the surgical site through the surgical corridor and monitoring the interbody with the x-ray machine. After the interbody has been implanted in the surgical site, the expansion band and the anchor 30 are removed from the surgical site. For example, the shim remover 38 is introduced into the surgical corridor between the retractor blades 16, slid down the surgical corridor, engaging the gripping member 38a with the receiving feature 20b, and withdrawing the shim remover 38 with the expansion band 20 and anchor attached thereto from the retractor 12.

Accordingly, a retractor system with retractor blades that do not interfere with x-ray viewing of an interbody being implanted within a surgical site, while at the same time withstanding the musculature load so as to maintain a uniform surgical corridor, is provided.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination.

The invention claimed is:

1. A retractor system for use in a spinal surgical procedure comprising:
   a retractor with a retractor blade support having at least two retractor blade slots and at least two retractor blade locking mechanisms;
   at least two retractor blades, each of the at least two retractor blades having a blade arm and a distal end, the blade arm dimensioned to fit at least partially within one of the least two retractor blade slots; and
   a shim and a shim inserter, the shim having an expansion band and an anchor configured to penetrate a vertebra or annulus of an intervertebral disc, the expansion band being a continuous member bounding an area and extending radially from a top portion of the anchor, the shim inserter configured to slide the shim between and along the at least two retractor blades and dispose the shim at the distal end of the at least two retractor blades;
   wherein the shim spreads the at least two retractor blades away from each other when the shim inserter slides the shim between and along the at least two retractor blades and the shim prevents the distal end of each of the at least two retractor blades from closing in on each other when the shim is disposed at the distal end of the at least two retractor blades.

2. The retractor system of claim 1, wherein the shim inserter has a distal end with a lip configured to push the shim between and along the at least two retractor blades towards the distal end of the at least two retractor blades.

3. The retractor system of claim 1, wherein the expansion band has a sidewall with a proximal edge and a distal edge, the proximal edge being thicker that the distal edge such that the sidewall has a wedge shape that facilitates entry of the expansion band between the at least two retractor blades and spreading of the at least two retractor blades away from each other when the shim insert slides the shim between and along the at least two retractor blades.

4. The retractor system of claim 1, wherein the anchor has a pointed end configured to penetrate the vertebra or annulus of the intervertebral disc.

5. The retractor system of claim 1, wherein the anchor is detachable from the expansion band.

6. The retractor system of claim 1, further comprising a first shim with a first expansion band having a first circumference and a second shim with a second expansion band having second circumference, the second circumference being larger than the first circumference such that the second shim can slide over the first shim during a surgical procedure and providing an enlarge surgical corridor.

7. The retractor system of claim 1, wherein the at least two retractor blade locking mechanisms are configured to lock the at least two retractor blades to the retractor blade support after the shim is disposed at the distal end of the at least two retractor blades.

8. The retractor system of claim 7, wherein the blade arm of each of the at least two retractor blades has a slot and the least two retractor blade locking mechanisms extend through the retractor blade slots to lock the at least two retractor blades to the retractor blade support.

9. The retractor system of claim 8, wherein the retractor blade support has a bottom ring with at least two threaded apertures and each of the at least two locking mechanisms have a knob with a threaded shaft, the knobs configured to extend through the retractor blade slots of the blade arm, engage the at least two threaded apertures and lock the at least two retractor blades to the retractor blade support.

10. The retractor system of claim 9, wherein the knobs lock the blade arm of each of the at least two retractor blades to the bottom ring of the retractor blade support.

* * * * *